United States Patent
Dent et al.

(10) Patent No.: US 7,844,326 B2
(45) Date of Patent: Nov. 30, 2010

(54) ELECTROTRANSPORT DEVICE HAVING AN INTEGRALLY MOLDED RESERVOIR HOUSING

(75) Inventors: Wanda Faye Dent, Chanhassen, MN (US); J. Richard Gyory, Sudbury, MA (US); Michael Joseph Grace, Stacy, MN (US)

(73) Assignee: Alza Corporation, Vacaville, CA (US)

( * ) Notice: Subject to any disclaimer, the term of this patent is extended or adjusted under 35 U.S.C. 154(b) by 1357 days.

(21) Appl. No.: 10/327,328

(22) Filed: Dec. 20, 2002

(65) Prior Publication Data

US 2003/0199807 A1    Oct. 23, 2003

(51) Int. Cl.
*A61N 1/30* (2006.01)

(52) U.S. Cl. .................................................. 604/20

(58) Field of Classification Search ............ 604/20, 604/501; 435/173.5–176.7; 204/450; 439/86, 439/89–91, 180, 278, 909; 600/372, 394; 607/120
See application file for complete search history.

(56) References Cited

U.S. PATENT DOCUMENTS

| | | | |
|---|---|---|---|
| 3,656,027 A * | 4/1972 | Isley | 361/502 |
| 3,901,218 A * | 8/1975 | Buchalter | 600/392 |
| 4,027,664 A * | 6/1977 | Heavner et al. | 600/376 |
| 4,141,359 A | 2/1979 | Jacobsen et al. | |
| 4,215,696 A * | 8/1980 | Bremer et al. | 600/392 |
| 4,383,529 A | 5/1983 | Webster | |
| 4,911,688 A * | 3/1990 | Jones | 604/20 |
| 5,006,108 A | 4/1991 | LaPrade | |
| 5,047,007 A | 9/1991 | McNichols et al. | |
| 5,158,537 A | 10/1992 | Haak et al. | |
| 5,224,927 A | 7/1993 | Tapper | |
| 5,224,928 A | 7/1993 | Sibalis et al. | |
| 5,246,418 A | 9/1993 | Haynes et al. | |
| 5,254,081 A | 10/1993 | Maurer et al. | |
| 5,288,289 A | 2/1994 | Haak et al. | |
| 5,310,404 A | 5/1994 | Gyory et al. | |
| 5,320,598 A | 6/1994 | Haak et al. | |
| 5,395,310 A * | 3/1995 | Untereker et al. | 604/20 |
| 5,499,628 A * | 3/1996 | Wright | 600/385 |
| 5,503,335 A * | 4/1996 | Noakes et al. | 239/690 |
| 5,573,503 A | 11/1996 | Untereker et al. | |

FOREIGN PATENT DOCUMENTS

HU    218361    8/1994

OTHER PUBLICATIONS

International Search Report dated Aug. 25, 2003 for corresponding Appl. No. PCT/US 02/41192.

* cited by examiner

*Primary Examiner*—Nicholas D Lucchesi
*Assistant Examiner*—Christopher D Koharski
(74) *Attorney, Agent, or Firm*—Michael J. Atkins

(57) ABSTRACT

This invention relates to an electrotransport device, which incorporates a conductive element within the reservoir housing of the device, which permits electrical communication from within the housing to outside of the housing without the use of opening, which require various methods of sealing the openings against leaks and moisture.

13 Claims, 3 Drawing Sheets

ELECTROTRANSPORT DEVICE HAVING AN INTEGRALLY MOLDED RESERVOIR HOUSING

TECHNICAL FIELD

The present invention relates to a transdermal therapeutic agent delivery and sampling device having a reservoir housing having an electrically conductive element integrally molded within the generally non-conductive housing. This electrically conductive element allows an electrical connection to be made across the reservoir housing without physically passing cables or wires through an opening in the housing. This electrically conductive element permits an electrical connection between the controller and other electrical components, located outside of the reservoir housing, and the electrode which is mounted inside of or is part of the reservoir housing.

BACKGROUND ART

The term "electrotransport" refers generally to the delivery or extraction of a therapeutic agent (charged, uncharged, or mixtures thereof) through a body surface (such as skin, mucous membrane, or nails) wherein the delivery or extraction is at least partially induced or aided by the application of an electric potential. The electrotransport process has been found to be useful in the transdermal administration of many drugs including lidocaine, hydrocortisone, fluoride, penicillin, and dexamethasone. A common use of electrotransport is in diagnosing cystic fibrosis by delivering pilocarpine iontophoretically. The pilocarpine stimulates production of sweat. The sweat is then collected and analyzed for its chloride content to detect the presence of the disease.

Electrotransport devices generally employ two electrodes, positioned in intimate contact with some portion of the body, typically the skin. A first electrode, called the active or donor electrode, is used to deliver the therapeutic agent into the body. The second electrode, called the counter or return electrode, closes an electrical circuit with the first electrode through the body. A source of electrical energy, such as a battery, supplies electric current to the body through the electrodes. For example, if the therapeutic agent to be delivered into the body is a positively charged cation, the anode is the active electrode and the cathode is the counter electrode required to complete the circuit. If the therapeutic agent to be delivered is a negatively charged anion, the cathode is the donor electrode and the anode is the counter electrode.

A widely used electrotransport process, electromigration (also called iontophoresis), involves the electrically induced transport of charged ions (e.g., drug ions) through a body surface. Another type of electrotransport, called electroosmosis, involves the trans-body surface (e.g., transdermal) flow of a liquid under the influence of the applied electric field. Still another type of electrotransport process, called electroporation, involves forming transiently existing pores in a biological membrane by applying high voltage pulses. In any given electrotransport system, one or more of these processes may occur to some extent simultaneously.

Most transdermal electrotransport devices have an anodic and a cathodic electrode assembly. Each electrode assembly is comprised of an electrically conductive electrode in ion-transmitting relation with an ionically conductive reservoir which is placed in contact with the patient's skin during use. A hydrogel reservoir such as described in Webster, U.S. Pat. No. 4,383,529 is the preferred form of reservoir since hydrated gels are easier to handle and manufacture than liquid-filled reservoirs. Water is by far the preferred liquid solvent for use in such reservoirs. This is in part because many drug salts are water-soluble and in part because water has excellent biocompatability, making prolonged contact between the reservoir and the skin acceptable from an irritation standpoint.

The term "agent" is intended to have its broadest interpretation and is used to include any therapeutic agent or drug, as well as any body analyte, such as glucose. The terms "drug" and "therapeutic agent" are used interchangeably to refer to any therapeutically active substance that is delivered to a living organism to produce a desired, usually beneficial, effect. This includes therapeutic agents in all the major therapeutic areas including, but not limited to: anti-infectives such as antibiotics and antiviral agents; analgesics, including fentanyl, sufentanil, remifentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

Of particular interest in transdermal delivery is the delivery of analgesic drugs for the management of moderate to severe pain. Control of the rate and duration of drug delivery is particularly important for transdermal delivery of analgesic drugs to avoid the potential risk of overdose and the discomfort of an insufficient dosage. One class of analgesics that has found application in a transdermal delivery route is the synthetic opiates, a group of 4-aniline piperidines. The synthetic opiates, e.g., fentanyl and certain of its derivatives such as sufentanil, are particularly well suited for transdermal administration. These synthetic opiates are characterized by their rapid onset of analgesia, high potency, and short duration of action. They are estimated to be 80 and 800 times, respectively, more potent than morphine. These drugs are weak bases, i.e., amines, whose major fraction is cationic in acidic media.

Electrotransport devices use at least two electrodes that are in electrical contact with some portion of the skin, nails, mucous membrane, or other surface of the body. One electrode, commonly called the "donor" electrode, is the electrode from which the therapeutic agent is delivered into the body. The other electrode, typically termed the "counter" electrode, serves to close the electrical circuit through the body. For example, if the therapeutic agent to be delivered is a positively charged cation, then the anode is the donor electrode, while the cathode is the counter electrode, which serves to complete the circuit. Alternatively, if a therapeutic agent is a negatively charged anion, the cathode is the donor electrode and the anode is the counter electrode. Additionally, both the anode and cathode may be considered donor electrodes if both anionic and cationic therapeutic agent ions, or if uncharged dissolved therapeutic agent, are to be delivered.

Furthermore, electrotransport delivery systems generally require at least one reservoir or source of the therapeutic agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more therapeutic agents or drugs. Electrotransport devices are powered by an electrical power source such as one or more batteries. Typically, at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; and the Webster Sweat Inducer, model 3600, sold by Wescor, Inc. of Logan, Utah) have generally utilized a desk-top electrical power supply unit and a pair of skin contacting electrodes. The donor electrode assembly contains a drug solution while the counter electrode assembly contains a solution of a biocompatible electrolyte salt. The power supply unit has electrical controls for adjusting the amount of electrical current applied through the electrodes. The "satellite" electrodes are connected to the electrical power supply unit by long (e.g., 1-2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al., U.S. Pat. No. 4,141,359 (see FIGS. 3 and 4); LaPrade, U.S. Pat. No. 5,006,108 (see FIG. 9); and Maurer et al., U.S. Pat. No. 5,254,081.

More recently, electrotransport delivery devices have become much smaller, particularly with the development of miniaturized integrated circuits and more powerful light weight batteries (e.g., lithium batteries). The advent of inexpensive miniaturized electronic circuitry and compact, high-energy batteries has meant that the entire device can be made small enough to be unobtrusively worn on the skin of the patient, under clothing. This allows the patient to remain fully ambulatory and able to perform all normal activities, even during periods when the electrotransport device is actively delivering drug. Such small self-contained electrotransport delivery devices are disclosed for example in Tapper, U.S. Pat. No. 5,224,927; Sibalis et al., U.S. Pat. No. 5,224,928; and Haynes et al., U.S. Pat. No. 5,246,418.

Reference is now made to FIG. 1 which depicts an exploded view of an exemplary electrotransport device 10 having an activation switch in the form of a push button switch 12 and a display in the form of a light emitting diode (LED) 14. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 may have lateral wings 15, which assist in holding device 10 on a patient's skin. Upper housing 16, when molded with the lateral wings, is generally composed of rubber or other elastomeric material, such as an ethylene vinyl acetate (EVA), silicone, polyolefinic elastomers (Engage®), or similar material. Upper housing 16, if not molded with the lateral wings, could be made of a more rigid material such as styrene, polypropylene, polyethylene or other similar material. Lower housing 20 is typically composed of a plastic or elastomeric sheet material (such as polyethylene terephthalate glycol (PETG) or polyethylene) which can be easily molded or thermoformed to form depressions for the reservoirs and the electrodes. The sheet material can easily be cut to form openings 23 and 23' therein. Alternately the lateral wings can be an integral part of the lower housing. In this case, the lower housing may be molded using an elastomeric material or thermoformed using a flexible material. Printed circuit board assembly 18 comprises an integrated circuit 19 coupled to discrete electrical components 40 and battery 32. Circuit board assembly 18 is attached to housing 16 by posts (not shown in FIG. 1) passing through openings 13a and 13b, the ends of the posts being heated and/or melted in order to heat stake the circuit board assembly 18 to upper housing 16. Alternate forms of assembly include the use of snap fit components, ultrasonic welding, screws, rivets or friction fit. Lower housing 20 is attached to the upper housing 16 by means of adhesive 30, the upper surface 34 of adhesive 30 being adhered to both lower housing 20 and upper housing 16 including the bottom surfaces of wings 15, if present.

On the underside of circuit board assembly 18 is battery 32, which serves as the power source for the device and which may be a button cell battery, such as a lithium cell. The circuit outputs of the circuit board assembly 18 make electrical contact with the electrodes 24 and 22 through openings 23, 23' in the depressions 25, 25' formed in lower housing 20 by means of electrically conductive adhesive 42, 42'. Electrodes 22 and 24, in turn, are in direct electrical and/or mechanical contact with the top sides 44', 44 of drug reservoir 26 and the non-drug containing electrolyte reservoir 28. The bottom sides 46', 46 of reservoirs 26, 28 contact the patient's skin through the openings 29', 29 in adhesive 30. Upon depression of push button switch 12, the electronic circuitry on circuit board assembly 18 delivers a predetermined direct current (DC) to the electrodes/reservoirs 22, 26 and 24, 28 for a delivery interval of predetermined length.

Electrotransport delivery devices are prepared, shipped, and stored (or stored, shipped, and stored), prescribed and then used. As a result, the devices must have components that have extended shelf lives that, in some instances, must comply with regulatory requirements. For instance, the U.S. Food and Drug Administration has shelf life requirements of from six to eighteen months or more for some materials. One complicating factor in achieving an extended shelf life is the stability of the system components when exposed to elevated temperatures. In order to achieve satisfactory dimensional stability of the elastomeric system components, the molding conditions as well as secondary manufacturing operations must be carefully optimized, requiring narrow ranges of process parameters, to avoid warpage, deformation and/or unacceptable dimensional changes. If the device housing should encounter elevated temperatures (i.e. over 40° C.) during storage or shipping these same undesirable deformations or dimensional changes may occur.

Further, electrotransport delivery devices typically contain electronic components (e.g., integrated circuits, resistors, diodes capacitors, inductors, etc.), conductive circuit traces, and electrical as well as physical connections therebetween which can corrode or otherwise be degraded by water or water vapor. Devices such as device 10 shown in FIG. 1 have hydratable or hydrated reservoirs 26, 28. Thus, humidity or moisture from the hydrated reservoirs can permeate or leak through the reservoir housing during manufacturing and storage. The moisture can thus cause corrosion of the electronic and/or mechanical components within the device, thereby reducing the shelf life of the device. One source of permeation or leaks is around the electrodes or around the electrical leads or contacts, which must supply electric current and voltage from the battery into the relatively wet environment inside of the reservoir housing.

In order to apply voltage from a power source to the donor reservoir, there must be some method or device used to place the power source in electrical communication with the donor reservoir.

One method is to mold, punch, drill, or in some other manner fabricate an opening in the housing used to contain the drug reservoir. An electrode is then placed or adhered on the inside of the housing, thus making the electrode accessible through the opening. The drug reservoir is then placed within the reservoir cavity so that it is in electrical contact with the electrode. Thereafter, electrical contact can be made with the drug reservoir via that portion of the electrode that is exposed by the opening in the reservoir housing.

There are several critical points in the implementation of this method. All of which involve sealing the opening in the reservoir housing. Because the drug reservoirs are often largely water, there is tendency for this liquid, moisture and/or humidity to escape from the housing and corrode the electronic and/or mechanical components if there is not proper sealing between the electrode and the drug reservoir housing. Because these devices are shipped and stored in sealed pouches, any water or moisture escaping from the reservoir will be trapped in the interior of the device and expose the controller circuitry and other electrical components to the water. Water, particularly water containing electrolyte salts which are typically found in the drug reservoir, can be very corrosive and quite damaging to the device.

One solution has been to develop dry or non-hydrated electrodes. See for example U.S. Pat. Nos. 5,158,537; 5,288,289; 5,310,404; and 5,320,598. Because the electrode only needs to be hydrated during actual use by the patient during drug delivery, the device can be manufactured and stored with the reservoir in a dry or non-hydrated state. Then a hydrating liquid, with or without the agent dissolved therein, is added to the reservoir just prior to use. But there are a number of design considerations that must be taken into account when this approach is used and it introduces its own set of challenges. Problems arise regarding dehydrating and rehydrating without damaging the drug reservoir and assuring the adequate and timely resolubilization of the active agent upon rehydration.

Other approaches have been to make the device resistant to moisture and corrosion. One step that has been taken to combat the corrosion problem has included gold plating the electrical and/or mechanical connectors (such as contacts or contact tabs) and circuit board traces. Such solutions are inherently expensive and add additional steps to the manufacturing process.

Other tactics used to deal with the moisture and corrosion problem has been to seal the electronics in a conformal coating, to package the hydrogel separately and to include desiccant in the pouch containing the device.

Use of conformal coatings requires an additional processing step which increases costs and production time. Packaging the drug reservoir gels separately also increases costs and production time and also includes additional steps for the patient who must then assemble the device prior to use. Desiccants in the device pouch also require additional components and also tend to dehydrate the gel reservoirs in the pouches which results in decreased efficiency when used by the patient.

DESCRIPTION OF THE INVENTION

The present invention provides an electrotransport reservoir housing having a conductive element integrally molded within the insulated housing. This integral molding enables placing the drug reservoir and electrode in electrical communication with the power source without the need for an opening in the reservoir housing. Because the molding process is performed at high heat and pressure, there is very tight, liquid and moisture impermeable bond between the material forming the reservoir housing and the conductive element. This results in a reservoir housing that is essentially a single integral component with no openings or other passages through the housing which would require subsequent sealing. By having a conductive element molded into the housing during manufacture, it eliminates problems of water and/or moisture from the drug reservoir contained within the interior of the reservoir housing leaking through or otherwise coming in contact with the electrical and/or mechanical components. In addition, the molded design allows electrical and/or mechanical connections to be formed as an integral part of the reservoir.

BRIEF DESCRIPTION OF THE DRAWINGS

A better understanding of the present invention as well as other objects and advantages thereof will become apparent upon consideration of the following detailed description especially when taken with the accompanying drawings, wherein like numerals designate like parts throughout, and wherein.

MODES FOR CARRYING OUT THE INVENTION

Figure 1:
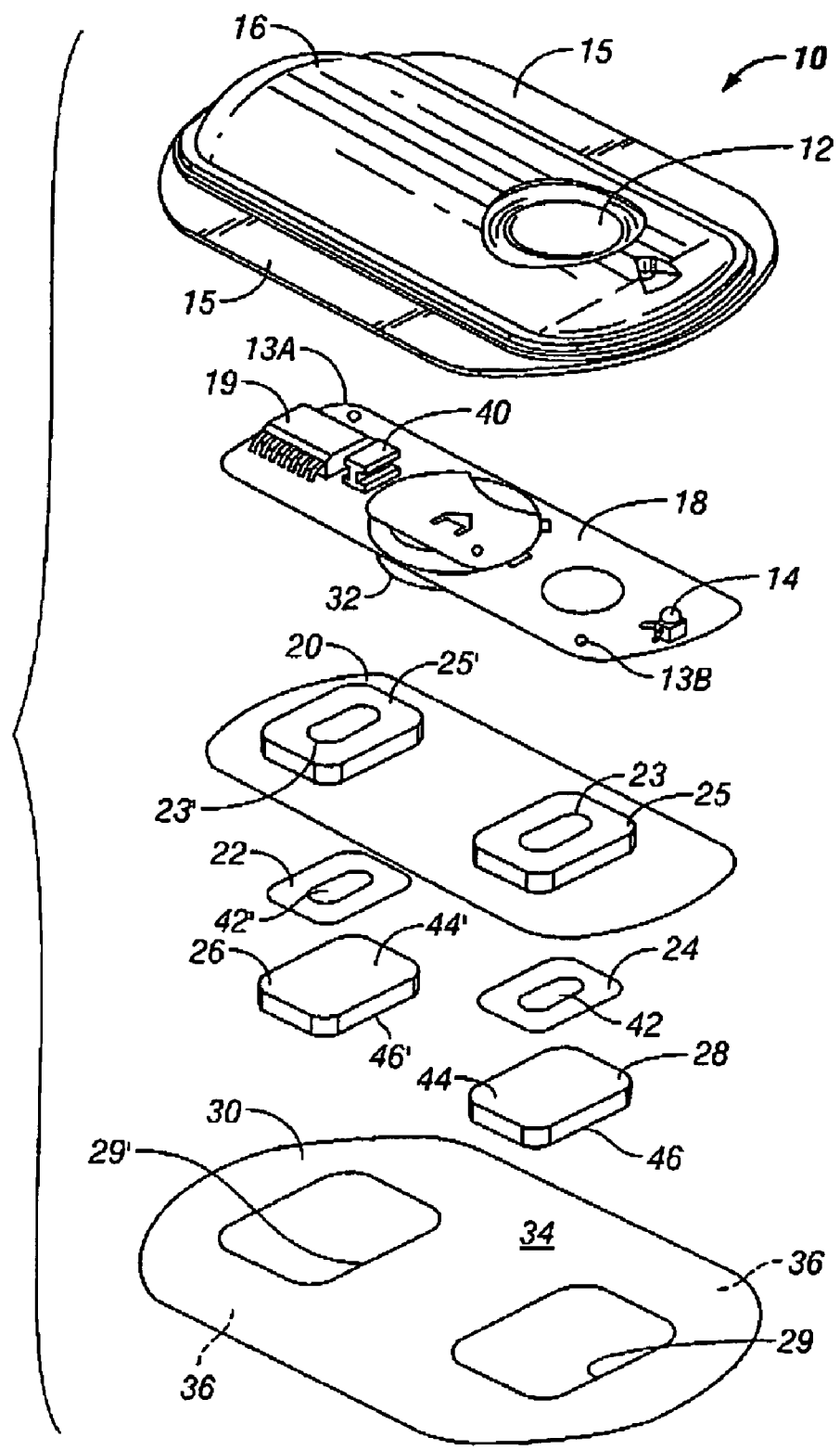
FIG. 1 is an exploded view of a prior art electrotransport device.
Figure 2:
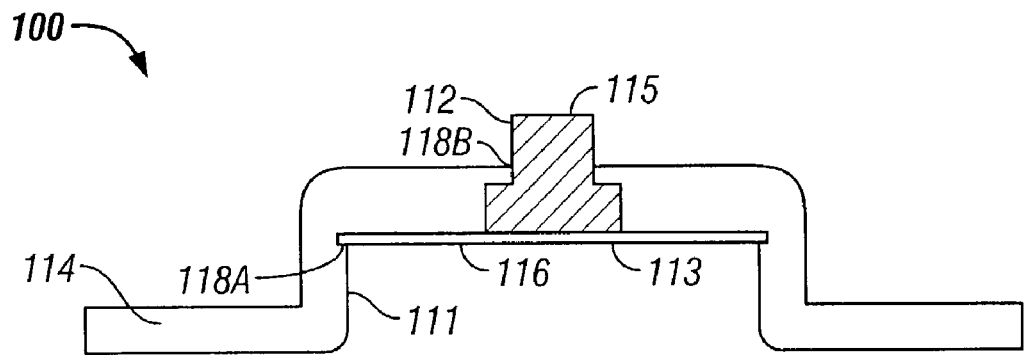
FIG. 2 is a perspective view of a generic embodiment of the invention including an electrode molded into the housing.

Reference is now made to drawings of an embodiment of the present invention, in particular FIG. 2. Reservoir Housing Assembly 100 is shown in perspective view. The bulk of the Reservoir Housing Assembly 100 is made up of Insulated Housing 114. The drug reservoir, not shown, would be placed within Reservoir Cavity 111 formed by Insulated Housing 114. In the middle of Insulated Housing 114 is Conductive Element 112. Conductive Element 112 is thicker than and extends beyond the surface of Insulated Housing 114. This provides an easily accessible contact pad or attachment point that can be used to electrically connect to an electrically conductive portion of a circuit board, battery, power source (not shown) or other electrical component.

Reservoir Housing Assembly 100 may be produced by a multi-shot injection molding process which forms Insulated Housing 114 around Conductive Element 112. Multi-shot injection molding is a known process in the art. It is a molding process that injects multiple materials into a single mold. In this case, the conductive plastic which is used to form the Conductive Element 112 is injected first into the mold and at the proper time (typically immediately or shortly afterwards), the non-conductive plastic used to form Insulated Housing 114 is then injected into the mold and around the already existing Conductive Element 112. It is possible to alter the order of injection and to first form Insulated Housing 114 and then inject the conductive plastic needed to from Conductive Element 112. The particulars of mold design and mold fabrication and the actual multi-shot injection molding process are well known or easily determined by one skilled in the art.

Inner Surface 113 of Conductive Element 112 is exposed within Reservoir Cavity 111. Outer Surface 115 of Conductive Element 112 is exposed on the outside of Insulated Housing 114.

This embodiment shows Electrode 116 after having been incorporated into the Reservoir Housing Assembly 100 by using an insert molding technique which is now described. This process requires placing Electrode 116 into the mold at the start of the molding process. The plastics that are injected during the subsequent injection molding steps flow around Electrode 116 and cause it to be secured in the bottom of Reservoir Cavity 111 and sealed within at Seal 118A. The conductive plastic flows behind the exposed surface of Electrode 16 making simultaneous contact with both Electrode 116 and Insulated Housing 114 and thus forming Conductive Element 112. This results in an electrical and mechanical bond between Electrode 116 and Conductive Element 112. Because Insulated Housing 114 was injection molded around Conductive Element 112 and Electrode 116, Seal 118A and 118B were formed by the interaction of the plastics and/or the geometry of the plastics. Seals 118A and 118B prevent leakage of water and/or water vapor from the drug reservoir, which is often an aqueous solution or aqueous gel and which is placed within Reservoir Cavity 111 sometime prior to use by the patient. A release liner (not shown), not only protects the drug reservoir but further acts as a seal to keep the reservoir gel hydrated between the time of manufacture and actual use by the patient. The release liner would be removed just prior to application of the electrotransport device to the skin of the patient.

For purposes of clarity, the remaining figures do not show the Electrode 16 molded in the housing. However, it is within the scope of this invention that all embodiments shown in FIGS. 3-6, could easily be modified to include an electrode molded into the reservoir. If Electrode 116 is not molded in the housing, then the electrode can be appliqued into the bottom of Reservoir Cavity 111 by standard techniques such as those which use electrically conductive adhesive tape (ECAT).

The conductive element can be any material which can be compounded with carbon black and subsequently co-extruded and thermoformed. Such materials include without limitation such polymers as polyvinyl chloride (PVC), polyethylene terephthalate glycol (PETG), polyethylene (PE), polypropylene (PP), polycarbonate (PC), acrylics, and similar materials. The range of resistivity suitable for the conductive material is less than about 10,000 ohms-cm, which can be achieved by compounding the polymer with at least 3 vol. % of various carbon blacks. The actual volume percent of carbon black used depends upon both the grade of the carbon black and target resistivity of the particular material being produced. The insulated housing should be composed of a material having a resistivity of $10^9$ ohms-cm or greater.

Figure 3:
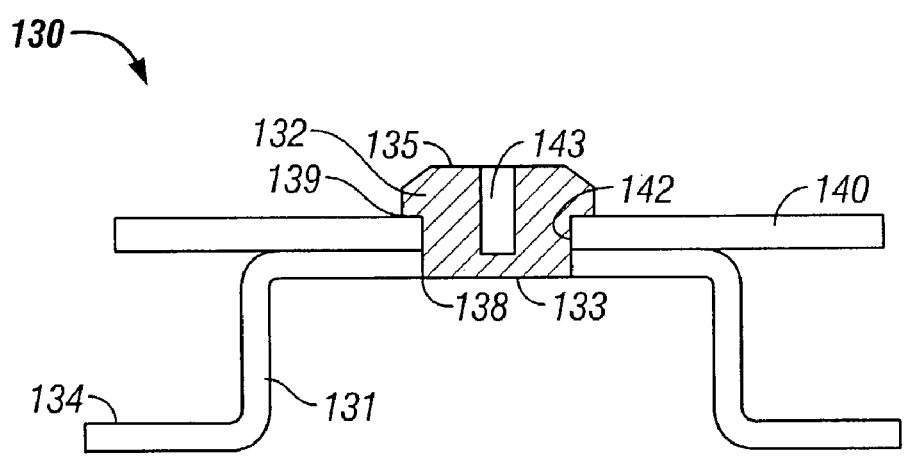
FIG. 3 is a perspective view of a specific implementation of the invention.

FIG. 3 shows Reservoir Housing Assembly 130 having a different configuration of the Conductive Element 132. In a manner similar to that already described, Insulated Housing 134 is multi-shot injection molded around Conductive Element 132 which forms a water and water vapor tight interface at Seal 138. Conductive Element 132 is shown with the Outer Surface 135 of the element tapered and having a Slot 143 molded into Conductive Element 132. In addition, Conductive Element 132 is molded from a semi-rigid or flexible material, which can be deformed and yet spring back and assume its original shape. This deformation is aided by the presence of Slot 143. The tapered profile, choice of materials, and slot permit Printed Circuit Board 140 to be electrically and/or mechanically attached to the Insulated Housing 134 by forcing the Conductive Element 132 through Opening 142 in the Printed Circuit Board 140. Conductive Element 132 can be compressed and/or deformed so that it can fit through the Opening 142 in Printed Circuit Board 140. Then it expands back to its original shape so that it extends over and retains Printed Circuit Board 140 in mechanical contact with Insulated Housing 134. In addition, electrical contact is made between Trace 139 on Printed Circuit Board 140 and the Conductive Element 132. As a consequence, Printed Circuit Board 140 is placed in electrical communication with Inner Surface 133 of Conductive Element 132 and further in electrical communication with an electrode and drug reservoir (not shown) that would usually be placed into the bottom of Reservoir Cavity 131 and thus in contact with Inner Surface 133.

Figure 4:
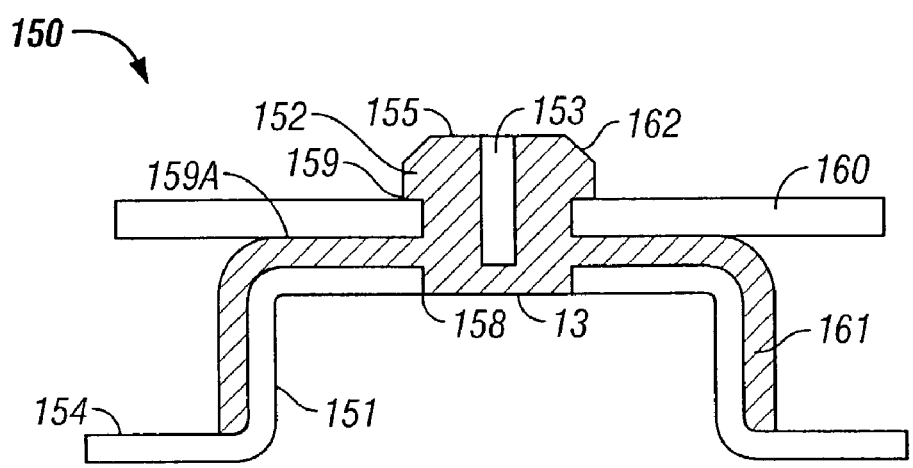
FIG. 4 is a perspective view of an embodiment similar to FIG. 2 which also includes an overmold applied to the housing.

FIG. 4 shows an embodiment similar to that of FIG. 3. The only difference is that Conductive Element 152 has been enlarged and now includes a peripheral portion that extends radially outwards and then extends downwards over Insulated Housing 154 to form Overmold 161. This overmold may provide additional structural support for Insulated Housing 154. Though Conductive Element 152 and Overmold 161 are shown in the drawing as a single element, the Overmold 161 could be fabricated from a different plastic and could even be non-conductive. Because Overmold 161 serves a different purpose than Conductive Element 152, its physical properties can chosen in order to satisfy separate design requirements.

Because both surfaces of Printed Circuit Board 160 make contact with Conductive Element 152 and/or Overmold 161, Conductive Element 152 and/or Overmold 161, if made of conductive material, can be in electrical communication with Trace 159 and/or Trace 159A which are positioned on opposite sides of Printed Circuit Board 160.

In the same manner as that shown in FIG. 3, Conductive Element 152 can be deformed, aided by the presence of Slot 153, and inserted through Opening 162 in Printed Circuit Board 160, thus retaining Circuit Board 160 mechanically and electrically.

Figure 5:
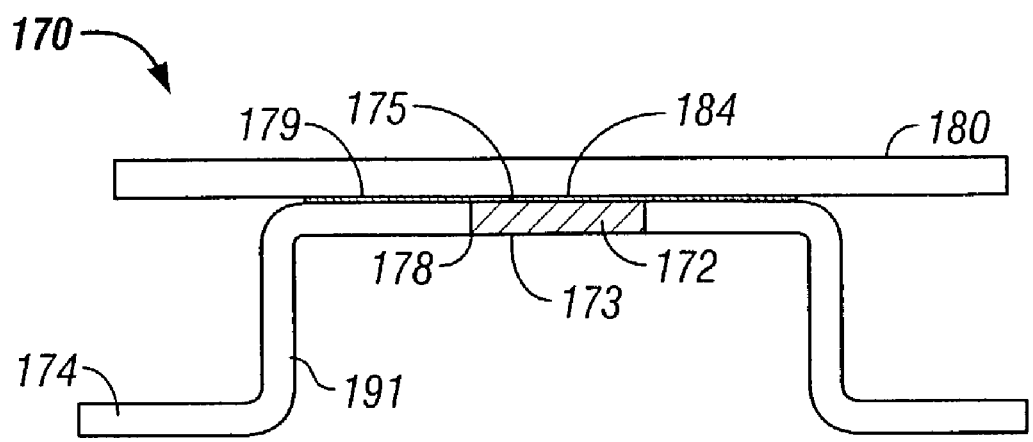
FIG. 5 is a perspective view of a additional embodiment using conductive adhesive.

FIG. 5 shows a simpler embodiment. Conductive Element 172 is approximately the same thickness as Insulated Housing 174. When Reservoir Housing Assembly 170 is fabricated, Insulated Housing 174 is injection molded around Conductive Element 172 forming Seal 178. Electrical communication and/or mechanical connection is established between Inner Surface 173 and Trace 179 on Printed Circuit Board 180 by attaching Printed Circuit Board 180 to Outer Surface 175 by using electrically conductive Adhesive 184, which could includes, but is not limited to silver epoxy and/or ECAT.

Figure 6:
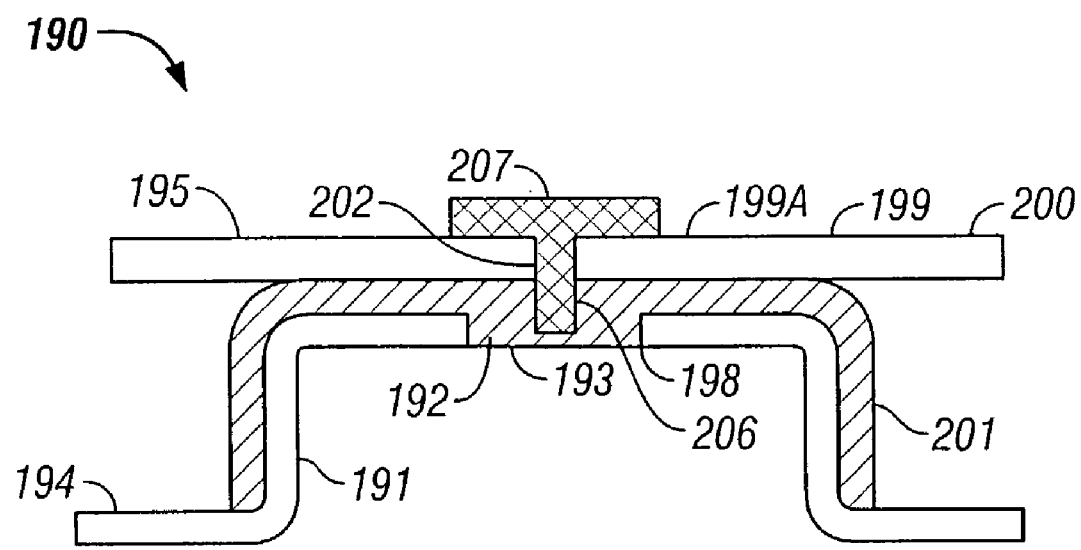
FIG. 6 is a perspective view of another embodiment, which includes both a conductive element in the housing and an conductive pin which is optionally conductive on the printed circuit board, as well as an optional overmold applied to the housing.

FIG. 6 shows a perspective view of another embodiment of the invention, which is represented by Reservoir Housing Assembly 190. The bulk of Reservoir Housing Assembly 190 is made up of Insulated Housing 194 which is injected molded around Conductive Element 192 forming Seal 198. Conductive Element 192 contains Pin Receiving Cavity 206 molded into the Outer Surface 195. Conductive Element 192 as shown includes an optional peripheral portion that extends radially outwards and then extends downwards over Insulated Housing 194 to form Overmold 201. This overmold provides additional structural support for Insulated Housing 194. Though shown in the drawing as a single element, the overmold portion could be fabricated from a different plastic and could even be non-conductive. Because Overmold 201 serves a different purpose than Conductive Element 192, its physical properties could be chosen in order to satisfy separate design requirements.

Printed Circuit Board 200 is mechanically and electrically attached to Conductive Element 192 and mechanically attached to Insulated Housing 194 by insertion of Pin 207 through Opening 202 in Printed Circuit Board 200 and into Pin Receiving Cavity 206. Because Pin 207 is typically constructed of conductive material, there is electrical communication between Pin 207 and Trace 199 located on one surface of Printed Circuit Board 200 and Trace 199A located on the other side of Printed Circuit Board 200. In addition, there is electrical communication between Pin 207 and Conductive Element 192. Trace 199 and Trace 199A are in electrical communication with other electrical elements and other traces that are part of Printed Circuit Board 200. Therefore, there is electrical communication between the electrical components on Printed Circuit Board 200, Trace 199 and/or Trace 199A, Conductive Element 192, and Inner Surface 193. As a consequence, If an electrode (not shown) is applied to the inside of Reservoir Cavity 191 it would be placed in electrical communication with Printed Circuit Board 200. Likewise, if a reservoir is placed in Reservoir Cavity 191, then the reservoir would be in electrical communication with the electrode, if present, and Inner Surface 193, Conductive Element 192, Overmold 201 (if conductive), Traces 199 and 199A, Conductive Pin Pin 207 and Circuit Board 200 and its electrical components.

Pin 207 is designed so that it forms a mechanical connection with Pin Receiving Cavity 206. Pin 207 can be a forced friction fit with Pin Receiving Cavity 206. Both Pin 207 and Pin Receiving Cavity 206 can be configured with mating parts to lock Pin 207 into Pin Receiving Cavity 206 when Pin 207 has been inserted a certain depth into Pin Receiving Cavity 206. Both Pin 207 and Pin Receiving Cavity 206 can be matingly threaded, with Pin Receiving Cavity 206 being sized and configured to receive the threads on Pin 207. Pin 207 could be a standard rivet that is mushroomed to retain it in the Pin Receiving Cavity 206. Further, Pin 207 can be physically separate from Printed Circuit Board 200 or it can be an integral part of Printed Circuit Board 200. Any number of other well-known means can be used to electrically and/or mechanically attach Pin 207 to Conductive Element 192.

Pin 207 could be made of conductive material so that a trace on the outside surface of Printed Circuit Board 200 could be placed in electrical communication with such a conductive Pin 207. For example, if Pin 207 were conductive, then Trace 199A, on the outside surface of Printed Circuit Board 200, would be in electrical communication with Pin 207, Conductive Element 192, Inner Surface 193 and any electrode or drug reservoir normally positioned in Reservoir Cavity 191. If Pin 207 were non-conductive, then only Trace 199 would be placed in electrical communication with Conductive Element 192 when Pin 207 was mechanically attached to Pin Receiving Cavity 206.

Though Conductive Insert 112, 132, 152, 172 and 192 are shown as a single integral component, it is within the scope of this invention that these elements may be comprised of a plurality of conductive and non-conductive subcomponents.

Though reservoir housing 114, 134, 154, 174, and 194 are shown as an integrated component comprising the Conductive Insert, it is within the scope of this invention that the reservoir housing may be comprised of a plurality of subcomponents in addition to the Conductive Insert.

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

The invention claimed is:

1. A reservoir housing for an iontophoretic drug delivery device comprising:
   a cavity and an interior and exterior surface; said reservoir housing at least partially formed of a non-conductive material; and
   a monolithic conductive element disposed within a portion of said reservoir housing, the monolithic conductive element integrally formed with the reservoir housing to provide a liquid and moisture tight interface between said conductive element and said reservoir housing.

2. The reservoir housing of claim 1, wherein said conductive element comprises a polymer.

3. The reservoir housing of claim 2, wherein said polymer is selected from the group consisting of polyvinyl chloride, polyethylene terephthalate glycol, polyethylene, polypropylene, -polycarbonate, and acrylics.

4. The reservoir housing of claim 3, wherein said conductive element further comprises carbon black.

5. A reservoir housing for an iontophoretic drug delivery device comprising:
   a cavity and an interior and exterior surface; said reservoir housing at least partially formed of a non-conductive material;
   a monolithic conductive element integrally formed within a portion of said reservoir housing to provide a moisture tight interface between said conductive element and said reservoir housing; said monolithic conductive element further comprising an inner and an outer surface and electrically accessible from both the interior and exterior surfaces of said reservoir housing; and
   an electrode disposed within said cavity, said electrode in electrical communication with the inner surface of said monolithic conductive element.

6. A reservoir housing for an iontophoretic drug delivery device comprising:
   a cavity and an interior and exterior surface; said reservoir housing at least partially formed of a non-conductive material;
   a monolithic conductive element integrally formed within a portion of said reservoir housing to provide a moisture tight interface between said conductive element and said reservoir housing;

said conductive element further comprising an inner and an outer surface and is electrically accessible from both the interior and exterior surfaces of said reservoir housing; and wherein said monolithic conductive element further comprises a central cavity and an outwardly extending lip, deformable and insertable through a correspondingly sized opening in an electrical component so that said electrical component can be inserted onto said deformable conductive element and releasably attached to said reservoir housing.

7. The reservoir housing for an iontophoretic drug delivery device of claim 6 wherein said outer surface of said monolithic conductive element is adapted to establish electrical communication with a circuit board when said circuit board is attached to said conductive element.

8. A reservoir housing for an iontophoretic drug delivery device comprising:

a cavity and an interior and exterior surface; said reservoir housing at least partially formed of a plastic, non-conductive material; and a plastic conductive element plastically bonded within a portion of said plastic, non-conductive material of said reservoir housing to provide a moisture tight interface between said plastic conductive element and said reservoir housing, said plastic conductive element having a volume resistivity less than about 10,000 ohms-cm.

9. The reservoir housing of claim 8, wherein said conductive element comprises a polymer.

10. The reservoir housing of claim 9, wherein said polymer is selected from the group consisting of polyvinyl chloride, polyethylene terephthalate glycol, polyethylene, polypropylene, -polycarbonate, and acrylics.

11. The reservoir housing of claim 10, wherein said conductive element further comprises carbon black.

12. A reservoir housing for an electrotransport drug delivery device comprising:

a cavity and an interior and exterior surface;

said reservoir housing at least partially formed of a non-conductive material; and a monolithic conductive element plastically bonded within a portion of said reservoir housing to provide a liquid and moisture impenetrable bond between said conductive element and said reservoir housing;

wherein said reservoir housing further comprises a seal portion to plastically or mechanically interact with said monolithic conductive.

13. A reservoir housing for an iontophoretic drug delivery device comprising:

a cavity and an interior and exterior surface;

said reservoir housing at least partially formed of a plastic, non-conductive material;

a conductive element plastically bonded within a portion of said reservoir housing to provide a moisture tight interface between said conductive element and said reservoir housing; and an electrode disposed within said cavity and plastically sealed to said reservoir housing, said electrode in electrical communication with a reservoir comprising a drug.

\* \* \* \* \*